July 27, 1954 H. C. SWIM Plant Pat. 1,291
ROSE PLANT
Filed June 29, 1953
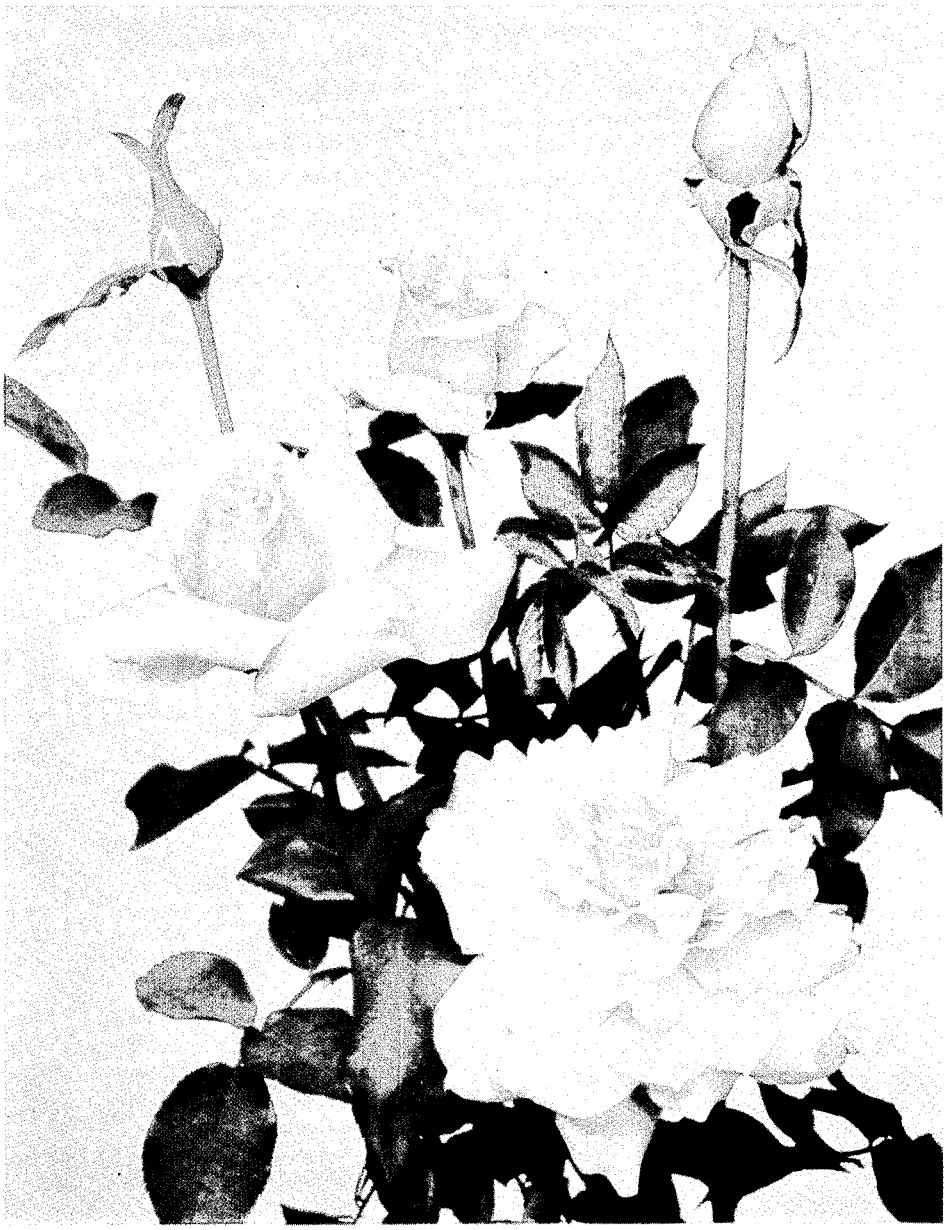
Inventor.
H. C. Swim
By: Robert Cobb
Attorneys.

Patented July 27, 1954

Plant Pat. 1,291

UNITED STATES PATENT OFFICE 1,291

ROSE PLANT

Herbert C. Swim, Ontario, Calif., assignor to Armstrong Nurseries, Inc., Ontario, Calif., a corporation of California Application June 29, 1953, Serial No. 364,974

1 Claim. (Cl. 47—61)

The present invention relates to a new and distinct variety of rose plant of the hybrid tea class, which was originated by me by crossing the well-known variety "Charlotte Armstrong" (Plant Patent No. 455) with the variety "Signora Piero Puricelli," better known in the United States as "Signora" (Plant Patent No. 201).

The primary objective in making this cross was to produce a new variety of rose plant which combines the best characteristics of the two parent varieties. This objective was fully achieved, as evidenced by the fact that my new variety is endowed with the following unique combination of outstanding characteristics:

(1) The various shades of orange color in the flowers, as derived from the pollen parent variety "Signora," but which shades are present in distinctively different proportions;

(2) The large flower size, as derived from the seed parent "Charlotte Armstrong," with many more petals than are found in the flowers of either parent;

(3) The strong, long and upright flowering stems, as inherited from "Signora";

(4) The glossy foliage that is characteristic of "Signora," but which is produced in the greater quantity that is characteristic of "Charlotte Armstrong"; and (5) The strong tea fragrance of the flowers which is much more pronounced than in the flowers of either parent.

In comparison with its seed parent "Charlotte Armstrong," the color of the blooms of my new variety is dominated by various shades of orange color, whereas the blooms of "Charlotte Armstrong" are light red and are specifically described as being from Spectrum red to cerise; the foliage of my new variety is glossy, whereas that of "Charlotte Armstrong" is dull and non-glossy; the blooms of my new variety have from 48 to 55 petals, and the petalage is much greater than that of "Charlotte Armstrong" which usually has from 30 to 35 petals per flower; and the flowers of my new variety have a strong fragrance, whereas those of this parent have only a slight fragrance.

As compared with its pollen parent "Signora," the plant of my new variety is much more branching and spreading in its habit of growth than "Signora," which has a more upright habit; the flowers of my new variety have a more pronounced fragrance than the flowers of "Signora" in which the fragrance is quite moderate; the foliage of the new variety is abundant and covers the plant well, whereas the foliage of "Signora"

is less abundant and does not cover the plant well; the peduncle of my new variety has very few prickles on its surface, whereas the peduncle of "Signora" has many prickles; and the petalage in my new variety runs from 48 to 55 petals and is classed as very double, whereas "Signora" has approximately one-half as many petals and is merely double.

Asexual reproduction of my new variety by budding at Ontario, California, shows that the foregoing characteristics and distinctions come true to form and are established and transmitted through succeeding propagations.

The accompanying drawing shows typical specimens of the flowers, foliage and stems of my new variety, with the colors thereof depicted as nearly true as it is reasonably possible to make the same in a color illustration of this character.

The following is a detailed description of my new variety, with color terminology in accordance with Robert F. Wilson's Horticultural Colour Chart (hereinafter identified as "Wilson") and with Ridgway's Color Standards and Nomenclature (hereinafter identified as "Ridgway"):

Type: Bush; outdoor; seedling; for cut flowers and for garden decoration.

Class: Hybrid tea.

Breeding: Seedling.

*Seed parent.*—"Charlotte Armstrong."

*Pollen parent.*—"Signora."

Propagation: Holds its distinguishing characteristics through succeeding propagations by budding.

*Flower*

Locality where grown and observed: Ontario, California.

Flowers borne: Usually singly; on strong, long stems.

Quantity of bloom: Very free, outdoors.

Continuity: Continuous during growing season.

Fragrance: Strong; tea.

Bud:

*Peduncle.*—Average length to long; average caliper to heavy; erect; numerous gland-tipped cilia and some prickles. Color—between Lettuce Green, Plate V (Ridgway) and Parrot Green, Plate VI (Ridgway).

*Before calyx breaks.*—Size—medium. Form—medium length; ovoid; with foliaceous appendages and numerous gland-tipped cilia on the surface of the bud; usually without much-cut foliaceous parts extending beyond the tip of the bud; sometimes with a single large foliaceous part extending beyond the tip of the bud equal to ½ or more of the length of the bud.

*As calyx breaks.*—Color—between Scarlet, Plate 19/1, page 19 (Wilson) and Geranium Lake, Plate 20/1, page 20 (Wilson), shaded somewhat with near Vermillion, Plate 18/1, page 18 (Wilson).

*Sepals.*—Inner surface—with fine, woolly tomentum. Margins—alternate sepals lined with white woolly tomentum; others lined with stipitate glands and some hairs.

*As first petal opens.*—Size—average to large. Form—medium length; ovoid to urn-shaped. Color—outside—near Vermillion, Plate 18/1, page 18 (Wilson), shaded with near Scarlet, Plate 19/1, page 19 (Wilson) and near Carmine, Plate 21/1, page 21 (Wilson); small area at base of petal near attachment near Lemon Yellow, Plate 4/1, page 4 (Wilson). Inside—between Orange, Plate 12/2, page 12 (Wilson) and Saturn Red, Plate 13/2, Page 13 (Wilson), shaded somewhat with near Tangerine Orange, Plate 9/2, page 9 (Wilson) and Mandarin Red, Plate 17/2, page 17 (Wilson); small area at base of petal near attachment near Lemon Yellow, Plate 4/1, page 4 (Wilson).

*Opening.*—Opens up well; is not retarded from opening by cold, hot, wet or dry weather.

Bloom:

*Size, when fully open.*—Large; 4 inches to 4¾ inches.

*Petalage.*—Very double; from 48 to 55 petals, plus 14 to 22 petaloids; arranged regularly.

*Form.*—High-centered at first; becoming open to somewhat cupped; petals being at first flat-cupped, with lateral margins reflexed ⅓ to ½ of upper portion of petal; outer petals sometimes reflexed ¾ of upper portion of petal; becoming later at maturity flat, with lateral margins reflexed ¾ or more of petal; apex reflexed slightly for ⅓ of petal length.

Petals:

*Texture.*—Medium thickness; only moderately leathery; with inside somewhat velvety and outside satiny.

*Shape.*—Outside—broadly obovate, with apex flat and rarely with 1 or 2 notches. Intermediate—obovate, with apex rounded to flat, and with rarely 1 to 2 notches. Inside—narrowly obovate; irregular, with apex rounded, and sometimes with 1 to 2 or 3 notches.

This description of a newly opened flower was made from a rose grown outdoors in the month of October, at Ontario, California:

*Color.*—Outside petal—outside surface—between Mandarin Red, Plate 17/2, page 17 (Wilson) and Vermillion, Plate 18/2, page 18 (Wilson), shaded somewhat with near Carmine, Plate 21/2, page 21 (Wilson), and with near Poppy Red, Plate 16/2, page 16 (Wilson); small area at base of petal near attachment near Lemon Yellow, Plate 4/2, page 4 (Wilson). Inside surface—between Orange, Plate 12/3, page 12 (Wilson) and Saturn Red, Plate 13/3, page 13 (Wilson); sometimes slightly marked especially near margins with near Carmine, Plate 21/2, page 21 (Wilson); small area at base of petal near attachment near Lemon Yellow, Plate 4/1, page 4 (Wilson). Intermediate petal—outside surface—between Mandarin Red, Plate 17/2, page 17 (Wilson) and Vermillion, Plate 18/2, page 18 (Wilson); small area at base of petal near attachment near Lemon Yellow, Plate 4/1, page 4 (Wilson). Inside surface — between Orange, Plate 12/2, page 12 (Wilson) and Saturn Red, Plate 13/2, page 13 (Wilson); small area at base of petal near attachment near Lemon Yellow, Plate 4/1, page 4 (Wilson). Inner petal — outside surface—between Mandarin Red, Plate 17/2, page 17 (Wilson) and Vermillion, Plate 18/2, page 18 (Wilson); small area at base of petal near attachment near Lemon Yellow, Plate 4/1, page 4 (Wilson). Inside surface—between Orange, Plate 12/2, page 12 (Wilson) and Saturn Red, Plate 13/2, page 13 (Wilson); small area at base of petal near attachment near Lemon Yellow, Plate 4/1, page 4 (Wilson).

This description was made from a rose that was open for three days outdoors in the month of October, at Ontario, Carifornia:

*Color.*—Outside petal — outside surface—near Mandarin Red, Plate 17/3, page 17 (Wilson), heavily shaded, particularly near margins, with between Carmine, Plate 21/3, page 21 (Wilson) and Crimson, Plate 22/3, page 22 (Wilson); small area at base of petal near attachment near Aureolin Plate 3/1, page 3 (Wilson). Inside surface—between Orpiment Orange, Plate 10/3, page 10 (Wilson) and Marigold Orange, Plate 11/3, page 11 (Wilson), shaded somewhat with near Carmine, Plate 21/3, page 21 (Wilson); small area at base of petal near attachment near Aureolin, Plate 3/1, page 3 (Wilson). Inside petal—outside surface—between Fire Red, Plate 15/3, page 15 (Wilson) and Poppy Red, Plate 16/3, page 16 (Wilson), shaded with near Mandarin Red, Plate 17/2, page 17 (Wilson) and striped sometimes with near Lemon Yellow, Plate 4/2, page 4 (Wilson); small area at base of petal near attachment near Lemon Yellow, Plate 4/2, page 4 (Wilson). Inside surface—between Marigold Orange, Plate 11/2, page 11 (Wilson) and Orange, Plate 12/3, page 12 (Wilson); small area at base of petal near attachment near Lemon Yellow, Plate 4/1, page 4 (Wilson).

*General color effect.*—Newly opened flower—between Saturn Red, Plate 13/2, page 13 (Wilson) and Nasturtium Red, Plate 14/2, page 14 (Wilson). 3 days open—between Orange, Plate 12/3, page 12 (Wilson) and Saturn Red, Plate 13/3, page 13 (Wilson), with marking of near Carmine, Plate 21/3, page 21 (Wilson) particularly on outer petals; small area at base of petal near attachment near Aureolin, Plate 3/1, page 3 (Wilson).

*Behavior.*—Drop off cleanly; not particularly affected by cold, hot, wet or dry weather.

*Flower longevity.*—On bush in garden—3 to 4 days in October. Cut roses grown outdoors kept at living-room temperatures—3 to 4 days in October.

*Reproductive organs*

Stamens: Average number; arranged regularly about pistils; a few mixed with petaloids.

Filaments: Medium length; 7 to 12 mm. in length; most with anthers. Color—between Mandarin Red, Plate 17/1, page 17 (Wilson) and Vermillion, Plate 18/1, page 18 (Wilson).

Anthers: Medium size to large; all open approximately at once. Color—upper side—margins between Lemon Yellow, Plate 4/2 page 4 (Wilson) and Buttercup Yellow, Plate 5/2, page 5 (Wilson); remainder between Canary Yellow, Plate 2/2, page 2 (Wilson) and Canary Yellow, Plate 2/3, page 2 (Wilson). Under side—margins between Lemon Yellow, Plate 4/2, page 4 (Wilson) and Buttercup Yellow, Plate 5/2, page 5 (Wilson); remainder between Canary Yellow, Plate 2/2, page 2 (Wilson) and Canary Yellow, Plate 2/3, page 2 (Wilson).

Pollen: Moderate to abundant. Color—between Indian Yellow, Plate 6/2, page 6 (Wilson) and Saffron Yellow, Plate 7/2, page 7 (Wilson).

Pistils: Many; approximately 130 in number.

Styles: Moderately even; average length; average caliper; somewhat loosely bunched; 4 to 8 mm. in length. Color—upper ⅓ between Scarlet, Plate 19/1, page 19 (Wilson) and Geranium Lake, Plate 20, page 20 (Wilson); remainder near Uranium Green, Plate 63/3, page 63 (Wilson).

Stigma: Color—near Aureolin, Plate 3/3, page 3 (Wilson).

Ovaries: Most enclosed in but some protruding from calyx.

Hips: Rarely sets hips.

Sepals: Permanent; medium length; recurved. Color—inside—between Lettuce Green, Plate V (Ridgway) and Parrot Green, Plate VI (Ridgway), masked by white woolly tomentum; outside—near Lettuce Green, Plate V (Ridgway).

Seeds: Rarely sets seeds.

*Plant*

Foliage:

*Leaves.*—Compound of usually 5 to 7 leaflets; abundant; medium size; leathery and glossy.

*Leaflets.*—Shape—ovoid, with acute apex and round base. Margin—simply serrate.

*Color.*—Mature: Upper surface—between Deep Dull Yellow-Green, Plate XXXII (1) (Ridgway) and Dark Dull Yellow-Green, Plate XXXII (Ridgway); under surface—between Turtle Green, Plate XXXII (Ridgway) and Chromium Green, Plate XXXII (Ridgway). Young: upper surface—near Cress Green, Plate XXXI (Ridgway), shaded with near Indian Red, Plate XXVII (Ridgway); under surface—between Mineral Red, Plate XXVII (Ridgway) and Indian Red, Plate XXVII (Ridgway).

*Rachis (the supporting stem of the compound leaf).*—Average size. Upper side—grooved; somewhat hairy and some stipitate glands on edges. Under side—prickly and with few stipitate glands.

*Stipules.*—Medium length; medium width, with medium length points usually turning out at an angle of 45° or less.

*Disease.*—More than average resistance to mildew, as compared with other varieties grown under comparable cultural conditions at Ontario, California.

Growth:

*Habit.*—Bushy; much-branched.

*Growth.*—Very vigorous.

*Canes.*—Medium caliper to heavy.

*Main stems.*—Color—near Absinthe Green, Plate XXXI (Ridgway). Large prickles—several; medium length; hooked slightly downward; with medium length to moderately long, narrow base. Color—between Mikado Brown, Plate XXIX (Ridgway) and Sayal Brown, Plate XXIX (Ridgway). Small prickles—very few. Color—near Sayal Brown, Plate XXIX (Ridgway). Hairs—none.

*Branches.*—Color—between Lettuce Green, Plate V (Ridgway) and Parrot Green, Plate VI (Ridgway). Large prickles—several; medium length; hooked slightly downward, with medium length to moderately long, narrow base. Color—between Tawny, Plate XV (Ridgway) and Russet, Plate XV (Ridgway). Small prickles—few. Color—between Tawny, Plate XV (Ridgway) and Russet, Plate XV (Ridgway). Hairs—none.

*New shoots.*—Color—near Lettuce Green, Plate V (Ridgway), shaded very slightly with near Hydrangea Red, Plate XXVII (Ridgway). Large prickles—several; medium length; hooked slightly downward; with medium length to moderately long, narrow base. Color—near Light Green-Yellow, Plate V (Ridgway), shaded with near Mineral Red, Plate XXVII (Ridgway). Small prickles—few to several. Color—near Light Green-Yellow, Plate V (Ridgway), shaded slightly with near Hydrangea Red, Plate XXVII (Ridgway). Hairs—none.

I claim:

A new and distinct variety of rose plant of the hybrid tea class, substantially as herein shown and described, characterized particularly as to novelty by the relatively large size and increased petalage of its flowers, by the strong, long and upright flowering stems thereof, by the distinctive various shades of orange coloring of its flowers, by the strong tea fragrance of its flowers, and by its abundance of glossy foliage.

No references cited.